(12) United States Patent
Paradis

(10) Patent No.: US 9,719,842 B2
(45) Date of Patent: Aug. 1, 2017

(54) METHOD FOR THE DISCOVERY, VALIDATION AND CLINICAL APPLICATION OF MULTIPLEX BIOMARKER ALGORITHMS BASED ON OPTICAL, PHYSICAL AND/OR ELECTROMAGNETIC PATTERNS

(71) Applicant: Norman A. Paradis, Putney, VT (US)

(72) Inventor: Norman A. Paradis, Putney, VT (US)

( * ) Notice: Subject to any disclaimer, the term of this patent is extended or adjusted under 35 U.S.C. 154(b) by 166 days.

(21) Appl. No.: 14/473,960

(22) Filed: Aug. 29, 2014

(65) Prior Publication Data

US 2015/0011844 A1 Jan. 8, 2015

Related U.S. Application Data

(63) Continuation-in-part of application No. 13/177,357, filed on Jul. 6, 2011, now abandoned.

(60) Provisional application No. 61/361,566, filed on Jul. 6, 2010.

(51) Int. Cl.
| | | |
|---|---|---|
| *G01N 33/48* | (2006.01) | |
| *G01G 19/44* | (2006.01) | |
| *A61B 5/00* | (2006.01) | |
| *A61B 8/08* | (2006.01) | |
| *G06F 19/00* | (2011.01) | |
| *G06G 7/58* | (2006.01) | |
| *G06F 19/24* | (2011.01) | |
| *A61B 5/0205* | (2006.01) | |

(52) U.S. Cl.
CPC ............ *G01G 19/44* (2013.01); *A61B 5/0059* (2013.01); *A61B 5/7264* (2013.01); *A61B 5/7275* (2013.01); *A61B 8/08* (2013.01); *G06F 19/345* (2013.01); *G06F 19/3431* (2013.01); *A61B 5/0075* (2013.01); *A61B 5/0205* (2013.01); *G06F 19/24* (2013.01)

(58) Field of Classification Search
CPC ..................................................... G06F 19/24
See application file for complete search history.

(56) References Cited

U.S. PATENT DOCUMENTS

| | | | |
|---|---|---|---|
| 2008/0114576 A1* | 5/2008 | Jackson | C12Q 1/6883 703/11 |
| 2008/0293047 A1* | 11/2008 | Pachot | C12Q 1/6883 435/6.11 |
| 2009/0208933 A1* | 8/2009 | Pachot | C12Q 1/6883 435/6.16 |
| 2012/0178111 A1* | 7/2012 | Diamandis | G01N 33/57423 435/7.92 |

* cited by examiner

*Primary Examiner* — Eric S Dejong

(57) ABSTRACT

A method for diagnosing or predicting the risk of shock, the method incorporating an algorithmic combination of optical, electromagnetic, and other sensors, along with their anatomic and temporal patterns. A method for developing the algorithms through iterative optimization using machine learning.

15 Claims, 1 Drawing Sheet

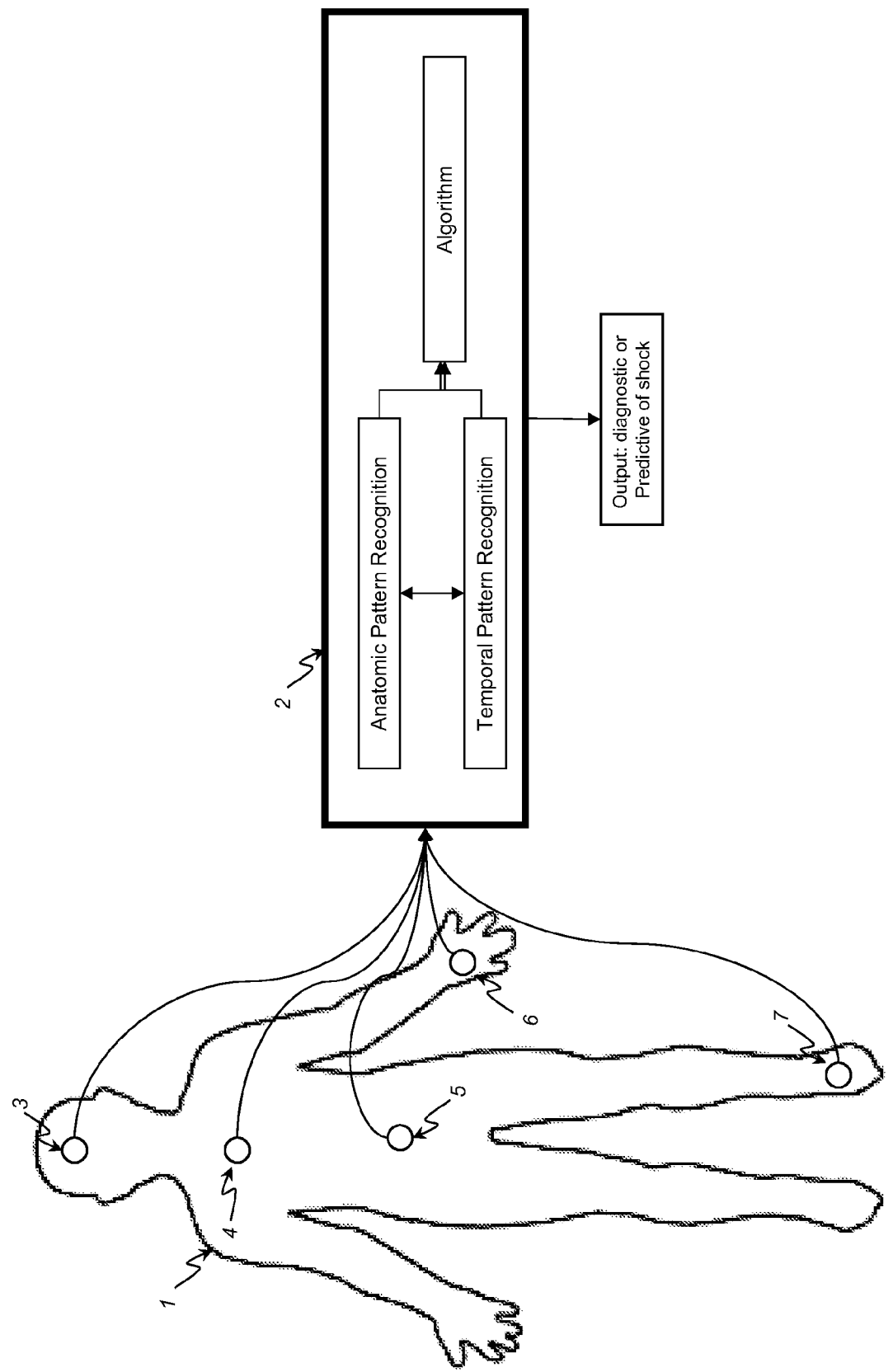

METHOD FOR THE DISCOVERY, VALIDATION AND CLINICAL APPLICATION OF MULTIPLEX BIOMARKER ALGORITHMS BASED ON OPTICAL, PHYSICAL AND/OR ELECTROMAGNETIC PATTERNS

BACKGROUND OF THE INVENTION

Field of the Invention

The invention disclosed here relates in general to the field of medical diagnostics, and more specifically methods for noninvasively diagnosing or predicting the risk of systemic medical conditions.

Description of the Related Art

Shock is the systemic pathophysiologic state characterized by organ perfusion inadequate to the tissues metabolic needs, and the organismal physiologic and pathophysiologic responses to this inadequate perfusion. At the tissue level, inadequate perfusion results in insufficient delivery of oxygen and metabolic substrate, and insufficient removal of waste products, including carbon dioxide.

The measurement of a patient's physical, chemical and anatomical properties is a central component of medical diagnosis. It has been appreciated by others that electromagnetic radiation may be directed into the body, and then transmitted or reflected energy used in medical diagnosis. The use of roentgen rays (i.e., electromagnetic radiation in the x-ray wavelengths) for production of diagnostic images is particularly well known. The body itself creates measurable electromagnetic fields, which are measured clinically by devices such as the electrocardiogram and electroencephalogram. Also known is the transmission, absorption, and/or reflectance of near-infrared and infrared wavelengths into tissues for the measurement of various molecular species and the state of cells and tissues, such as the use of near-infrared spectroscopy to measure oxygen saturation of hemoglobin. (Jobsis 1264-67)

When subjected to inadequate blood flow, tissues undergo a number of changes that may be detectable non-invasively using optical technologies. Among these are: decreased oxygen tension, increased carbon dioxide tension, decreased pH, altered energy metabolism, altered redox potential within the cytochrome. Additionally, there are alterations in the hemogram and hemodynamics that may be detectable, including the heart rate, hematocrit and red blood cell velocities. Some of the various molecular species that constitute the metabolome may also be measureable, in particular, the concentration of glucose.

Using electromagnetic potential or impedance it is also possible to measure, or more likely approximate, a number of clinically important measures of hemodynamics. Among these are cardiac output and ventricular stroke.

Importantly, it is likely that the measurement of tissue and organ parameters non-invasively has significant inaccuracy and the validity of the derived measurements in the setting of disease and hemodynamic instability may be limited. (Lewis et al. 1334-38) Such inaccuracy may underlie the limited adoption of single measurement non-invasive technologies clinically.

Previous to this disclosure, medical diagnostics based on physical measurements have generally been limited to the production of images, or the uniplex measurement of optical or physical properties of tissues or organs. Previously, optical measurements, such as tissue oxygen status have only been measured at single location on or within the body. The electrocardiogram has been traditionally measured at multiple locations, but these have been presented to clinicians only as a series of uniplex vectors.

Previous to this disclosure, it has not been appreciated that clinically useful diagnostic biomarkers for shock might be synthesized from multiple noninvasive optical measurements.

The present disclosure is for a system intended generally to predict the risk of, or assist in the diagnosis of, shock. Shock is the complex systemic pathophysiologic state generally characterized by organ perfusion inadequate to the tissues metabolic needs, and the organismal physiologic and pathophysiologic responses to this inadequate perfusion. Shock may be caused by any pathological process that interferes with hemodynamics, including hemorrhage, sepsis, or myocardial infarction. Depending on the degree of insult, and the adequacy of physiologic response, shock may be transient and reversible. If, however, the degree of insult is greater than the compensatory capacity of the organism, shock may become an unstable state that progresses to hemodynamic collapse and death.

Traditionally, biomarkers diagnostic or predictive of shock were pre-existing measured hemodynamic parameters that were used as surrogate indicators. In particular, these have included blood pressure, time for capillary refill, among others. These have been measured directly via catheters, or indirectly via acoustics. Regardless, the diagnostic inadequacy of traditional measurements is well-documented. (Cohn 118-22)

The limited utility of traditional measurements has led to the measurement of alternative indicators of hemodynamics, including cardiac output, ventricular stroke volume, and systemic vascular resistance. Again, these may be measured directly via catheters or indirectly via techniques such as impedance. However, similar to the traditional measurements of blood pressure, utilization of additional hemodynamic parameters has not provided an adequate solution to the diagnosis of shock.

The continuing need for earlier detection of shock is universally acknowledged by clinicians to be an important unmet need. In an e-mail from Baghdad dated Jun. 20, 2007 military physicians stated "there are three groups of casualties: 1) the ones who are really sick and (almost) everyone knows it; 2) the ones who have minimal injuries and will live almost regardless of what we do; 3) those who look like they aren't too bad but then deteriorate. (We are) most interested in identifying Group 3."

The poor performance of traditional markers has led to attempts to identify innovative tissue sensors with improved performance. Single biosensors for measurement of skin, tissue and visceral organ status utilizing existing technology such as pulse oximetry, near-infrared reflectance, Doppler flow have been extensively studied as possible early non-invasive detectors of shock.

Of note, all attempts to develop innovative tissue sensors have focused on the optimizing the measurement in one location. (Soller et al. 475-81) The possibility that improved diagnostic performance might be achieved by multiplex measurement of tissue parameters at multiple anatomic locations has not been previously considered.

Depending on the degree of insult, and the host physiologic response, the measurable tissue and organ parameters vary predictably as the shock state develops. The body attempts to spare vital organs, in particular the brain and heart, limiting early effects to non-vital organs such as the skin and digestive viscera. Measurements of tissue status will reflect these patterns in various organ. Physiologically distinct organ systems include: the central nervous system, the heart and arterial vasculature, the venous vasculature, the kidneys, skeletal musculature, the mucosa, the dermis and epidermis, among others. Even among these specific systems, shock may have variable anatomic effects. For instance, the effect on the dermis and epidermis may be different between the distal extremities, the trunk, and the head. The same would likely be true with respect to the skeletal musculature.

Although uniplex measurement of tissue parameters at single locations has proven inadequate in the development of diagnostic methods for shock, it may be appreciated that a great deal more information is available in the anatomic and temporal patterns of tissue measurements.

The present disclosure is for a system intended principally to predict the risk of, or assist in the diagnosis of the systemic disease of shock. As envisioned, multiple sensors are placed at physiologically distinct locations, and machine learning is utilized to derive algorithms that may combine optical, electromagnetic, anatomical and temporal inputs, among others, to create a synthetic biomarker that outperforms any single measurement clinically.

Recently, machine learning derived multiplex algorithms constructed from the measurement of multiple individual serum molecular concentrations have been widely studied as innovative in vitro diagnostics. (Kato 248-51) These same approaches, however, have not been applied in systemic disease to non-molecular measurements such as those based on electromagnetic or optical sensing.

As in molecular multivariate assays, it is widely appreciated that useful mathematical diagnostic algorithms may be developed using the in silico techniques variously called machine learning, data mining, and big data, among other terms. For the purposes of the present disclosure, the term "machine learning" will be used to represent all possible mathematical in silico techniques for creation of useful algorithms from large data sets. The term "algorithm" will be utilized in reference to the clinically useful mathematical equations or computer programs produced by the process disclosed. Particularly important to the present disclosure is the widely acknowledged phenomena that the performance of machine learning derived algorithms is independent of the specific in silico software routine used for its derivation. If the same training data set is used, techniques as different as supervised learning, unsupervised learning, association rule learning, hierarchical clustering, multiple linear and logistic regressions are likely to produce algorithms whose clinical performance is indistinguishable.

Although the techniques of machine learning are to a great extent interchangeable, it is well known to those skilled in the art that the independence of the individual variables used in the model is of great importance. Multiple variables will bring no additional diagnostic performance if they are highly correlated and essentially measure the same tissue parameter. With respect to the present invention, it is anticipated that the utilization of anatomic and temporal patterns of organ systems that are physiologically distinct in their response to impending shock will enhance the performance of the algorithm.

Any diagnostic method initially developed to diagnose disease may also be used to guide therapy. With respect to the present invention, the algorithm may also be optimized as an adjunct to resuscitation and treatment of shock. As such, it would function as a goal for directing therapy. Such targeted therapeutics are often called theranostics.

These and other objects, features and advantages of the present invention will become clearer when the drawings as well as the detailed description are taken into consideration.

Prior Art

There is no prior art teaching the use of temporal and anatomic patterns derived from the noninvasive measurement of tissue status in multiple physiologically distinct locations in a method for diagnosing or predicting the risk of shock.

The following comprehensive searches of the world wide web find no results: "multiple optical sensors for diagnosis of shock", "multiple electromagnetic sensors for diagnosis of shock", "multiple optical sensors for diagnostic of shock", "multiple electronic sensors for diagnostic of shock", "multiple optical sensors for prediction of shock", "multiple electromagnetic sensors for prediction of shock", "multiplex optical system for diagnosis of shock", "multiplex optical system for prediction of shock", "anatomic patterns in shock", "anatomic and temporal patterns in shock", A search for "a combination of electromagnetic and optical sensors" resulted in no citations within the life sciences.

Comprehensive Pubmed searches reveal the following: a title search combining "multiple" and "optical" and "shock" provides no results; a title search combining "multiple" and "optical" and "shock" provides 1 result which was unrelated to the subject matter of the present invention; a title search combining "multiplex" and "optical" provides 20 results, none of which teach a method remotely similar to the presently disclosed invention.

When utilization of multiple electromagnetic or optical sensors has been taught previously, the intent was directed not at systemic illness or shock, but local pathophysiologic events such as vascular occlusion or local tissue ischemia. In such proposed devices, the placement pattern of the sensors empirically reflects known anatomic structures, and the information derived is anatomically local in nature. For instance, the specific leads in the standard electrocardiogram are intended to indicate normality or injury in the area of the myocardium represented by specific vectors. Boyden et al (US2009/0281413A1) utilizes multiple optical sensors and statistical learning with the intention of identifying a vascular occlusive event. The optical arrays are proximal and distal to the possible occlusion and reflect known local vascular anatomy in a straightforward and deterministic manner.

Summary of Deficiencies in the Prior Art: 1) No non-invasive diagnostic methods for shock incorporate multiplex sensing; 2) No non-invasive diagnostic methods for shock incorporate multiplex optical sensing; 3) No non-invasive diagnostic methods for shock incorporate multiplex electromagnetic sensing; 4) No non-invasive diagnostic methods for shock incorporate multiplex sensing that combines optical and electromagnetic sensing; 5) No non-invasive diagnostic methods for shock incorporate multiplex sensing based on an optimized algorithm; 6) No non-invasive diagnostic methods for shock that algorithmically incorporate sensing in multiple physiologically distinct anatomic location; 7) No non-invasive diagnostic methods for shock that algorithmically incorporate temporal patterns; 8) No non-invasive diagnostic methods for shock that algorithmically incorporate combination of anatomic and temporal patterns; 8) No non-invasive diagnostic methods for shock that algorithmically incorporate combination of anatomic and temporal patterns with traditional measurements such as the electrocardiogram.

SUMMARY OF THE INVENTION

A method for diagnosing or predicting the risk of shock, the method incorporating an algorithmic combination of optical, electromagnetic, and other sensors, along with their anatomic and temporal patterns. A method for developing the algorithms through iterative optimization using machine learning.

BRIEF DESCRIPTION OF THE DRAWINGS

For a fuller understanding of the nature of the present invention, reference should be had to the following detailed description taken in connection with the accompanying drawings in which:

FIG. 1 is a diagrammatic representation of one embodiment of the method for the discovery, validation and clinical application of multiplex biomarker algorithms based on optical, physical and/or electromagnetic patterns

DETAILED DESCRIPTION OF THE PREFERRED EMBODIMENT

The present disclosure is for a system intended generally to predict the risk of, or assist in the diagnosis of, shock.

It will be appreciated that the present disclosure is for two components of the method:
1) A method useful for diagnosing or predicting the risk of shock, the method incorporating an algorithmic combination of optical, electromagnetic, and other sensors, along with their anatomic and temporal patterns.
2) A discovery method useful for developing the algorithms described in 1) through iterative optimization using machine learning.

A preferred implementation of the method used diagnostically:

Placement of sensors in a combination of physiologically distinct locations so as to obtain physiologically independent input data. Such locations would include a combination of: the cranium, the neck, the thorax, the abdomen, one or more extremities, among others.
1. The combination of specific locations sensing would include the standard electrocardiogram positions as clinicians generally place sensors in these positions in critically ill patients.
2. Additional specific locations would include one or more surface locations which provide noninvasive access to visceral organs, such as over the kidney or liver.
3. It is anticipated that input data would be obtained noninvasively from the: central nervous system, circulatory system, skeletal musculature, skin, and visceral organs.
4. The sensor array would include a combination of following components: an electrode for measurement of electrical potential and electrical impedance, an optical detector for measurement of photons, a light emitter for transmission of light into the tissues.
5. Measurements that would include a combination of tissue state parameters and hemodynamics measured by optical spectroscopy and electromagnetic potential and impedance.
6. The algorithms would include anatomic and temporal patterns among the sensory data.
7. In addition to the anatomic and sensory data patterns, the algorithms would include one or more of measured or derived physiologic variables, including: heart rate and pattern, blood pressure and pattern, cardiac output and stroke volume derived from impedance, tissue oxygenation, tissue pH, hemoglobin and cytochrome oxygenation reduction status, hematocrit.
8. Anatomic patterns that would be used in the algorithm would include one or more of: craniosacral, axial-appendicular, skeletal-visceral, cranial-skeletal, cranial-visceral.
9. Temporal patterns that would likely be used in the algorithm would include one or more of: stable and unchanged, baseline to present, increasing or decreasing instability, accelerating deterioration, stabilizing deterioration, improvement.
10. The methods would likely include a combination of sensor locations sufficient to measure the status of a plurality of the central nervous system, cardiovascular system, musculoskeletal and visceral organ systems.
11. The algorithm would convert the complex input data into a simpler index for use by clinicians.

A practitioner skilled in the art would, once taught the invention, would know that the essential components of invention include:
1. A synthetic biomarker diagnostic or predictive of shock.
2. The biomarker is a multiparametric algorithm or equation that includes the anatomic and/or the temporal pattern of optical or electromagnetic measurements at multiple physiologically distinct locations on or within the patient's body.

There are components of the invention that, while sufficient, are interchangeable within the context of the invention. A practitioner skilled in the art would know which specific embodiments of these components to test in optimizing performance of the invention:
1. Specific sensors—type and wavelength of the optical and electromagnetic sensors
2. Exact locations on or within the body
3. Machine learning software used for discovery and development—regression, neural network, etc.
4. Mathematical structure of the algorithm or equation developed by the machine learning The first method taught is that of the synthetic biomarker. The second method is for the discovery, development, and validation of the biomarker, the method comprising:
1) measuring the optical, electromagnetic, or physical properties at multiple physiologically distinct locations on or within the body in the setting of experimentally induced or clinically occurring disease;
2) using known machine learning techniques to derive a multiparametric prognostic or diagnostic algorithm that include, among other variables, anatomic or temporal patterns of optical, electromagnetic, or physical measurements, such that the algorithm has better clinical performance than any of the input parameters individually;
3) optimizing the algorithm iteratively using additional clinical data sets, clinical classifiers, along with patient characteristics and laboratory derived measurements as needed;
4) transforming the output results of the algorithm to a uniplex numerical or visual scale or index that is a probabilistic biomarker indicative of the risk or presence of the disease.

Specifically, as shown in FIG. 1, sensors measuring the optical, electromagnetic, or physical properties of tissues are placed at multiple physiologically distinct locations on or within the body in the setting of experimentally induced or clinically occurring disease. These sensors may be incorporated into standard sensors utilized by clinicians such as electrocardiogram, oxygen saturation at the finger, among others.

In this same embodiment, machine learning techniques are then utilized to derive a multiparametric prognostic or diagnostic algorithm that include, among other variables, anatomic or temporal patterns of optical, electromagnetic, or physical measurements, such that the algorithm has better clinical performance than any of the input parameters individually.

In this same embodiment, the algorithm is improved iteratively using additional clinical data sets, clinical classifiers, along with patient characteristics and laboratory derived measurements as needed.

In this same embodiment, the output results of the algorithm is transformed to a uniplex numerical or visual scale or index that is a probabilistic biomarker indicative of the risk or presence of the disease of interest.

As currently disclosed, the physical properties being measured may include, but are not limited to, photons, electromagnetic radiation (EMR), temperature, density, weight, hydration state, transmission of sound, etc., or any combination of these inputs (i.e., data measurements). Practitioners skilled in the art will be familiar with the complete range of potential physical properties that may be measured.

As currently disclosed, the physical energy, property or field measured may be intrinsically produced within the patient's body, but a particular embodiment is based on measurements derived from the transmission, and/or reflectance, and/or absorption, of energy from an external source. The absorption and/or transmission used may be florescence, reflectance or phosphorescence. As presently envisioned, the biomarker would not be an image.

As currently disclosed, electromagnetic radiation may be directed into the patient. This may be of any wavelength, but a particular embodiment is based on optical wavelengths selected for their ability to penetrate tissues and interact usefully with tissues, cells and molecular species of interest. The signal measured may be different from, but physically coupled with, the energy transmitted into the tissues, such as the photo-acoustical effect.

As known by practitioners skilled in the art, the probability of deriving clinically useful algorithms using the techniques of machine learning is enhanced if the number of input variables is increased and they are independent measures of pathophysiologically distinct information. Thus, as envisioned, the placement of sensors will be intended to obtain measurements in as many physiologically distinct location as possible. An incomplete list of physiologically distinct locations would include the surface of the head, neck, chest, abdomen, extremities and digits. For sensors that are able to obtain data from below the dermis, the list of locations would include, but not be limited to, regions over distinct muscle groups, portions of the central nervous system, and every visceral organ.

The in silico techniques used to create models and algorithms are well known to those familiar with the art. The numerous specific techniques may be categorized as supervised, unsupervised, reinforcement, and association rule learning, statistical classification, partition and hierarchical clustering, and deep learning techniques, among others. Among the most commonly used are the various forms of regression, including multiple linear and logistic regressions.

Particularly important to the present disclosure is the widely acknowledged phenomena that the performance of machine learning derived algorithms is to a great extent independent of the specific in silico technique used for its derivation. This is emphasized by the packaging of numerous techniques on in software packages, which may run some or all of them simultaneously on data sets.

Some of the machine learning techniques require a classifier. In development of clinical biomarkers the classifier is exemplified by separation of the training data set between patients with or without the disease of interest based on the use of a "gold standard" diagnostic test. An example of a gold standard test would be the use of cardiac echocardiography in the diagnosis of congestive heart failure.

In one embodiment of the invention, an input parameter is used to modify the pre-test probability distribution of other inputs of the mathematical model, or even the final multiplex algorithm. By way of example, but not limitation, the mathematics or computer code utilized to optimize the performance of surface temperature patterns as a diagnostic of infection or shock may be adapted as a function of different concentrations of blood lactate.

It should be appreciated that any individual input to the algorithm, or pattern of multiple inputs to the algorithm, may be used in combination with any other input to create a synthetic biomarker whose diagnostic performance is superior to that of the individual inputs. It will be appreciated by those expert in the development of multiplex algorithms that such development processes may be iterative.

It is anticipated that the first-pass algorithm discovery and optimization may be further optimized by inclusion of patient, clinical, hospital or epidemiology data as inputs to the machine learning process. A particular embodiment would be adaptation of the algorithm based on the results of proteomic, genomic or other in vitro diagnostic measurements.

It should also be appreciated that the biomarker pattern or algorithm may be adaptive, improving over time or as a function of feedback within a specific epidemiologically useful unit. For example, the biomarker algorithm may be different in hospitals whose incidence of the disease in question are different. Some of these inputs may be adaptable at the bedside, as for instance, the patient's age or sex. Some or all of the input parameters may also be obtained internally from the patient via tomography or imaging.

The biomarker algorithms may include measurements that are made after energy has been transmitted into the body. The energy administered to the patient may be of a different character than the measurement used in the biomarker algorithm. In certain particular embodiments, the electromagnetic source will be in a different location, such as in transillumination. These locations may include orifices, the gastrointestinal tract, the intravascular space, or other potential spaces.

Input data and patterns which may contribute to (i.e., be used in) the multiplex algorithm may include, but are not limited to, the anatomic pattern, the temporal pattern, a combination of anatomic and temporal patterns and the pattern of absorbance, transmission, reflectance, florescence, phosphorescence.

It is anticipated that the anatomic pattern may include multiple locations including axial, extremities, oral, conjunctiva, rectal, nasal, needle intra-tissue, and intravascular catheter based locations. Anatomic patterns that would be used in the algorithm would include one or more of: craniosacral, axial-appendicular, skeletal-visceral, cranial-skeletal, cranial-visceral. In a particular embodiment of the invention, the anatomic parameter of interest is depth below the skin, with different depths being used in different locations.

The temporal pattern is the change in one or more components over time. Practitioners skilled in the art of machine learning will know that different temporal patterns may be used in relation to differing inputs. Temporal patterns that would likely be used in the algorithm would include one or more of: stable and unchanged, baseline to present, increasing or decreasing instability, accelerating deterioration, stabilizing deterioration, improvement.

There are currently many types of electromagnetic, physical and optical measurements that may be utilized. Electromagnetic wavelengths and patterns may include optical, near infra-red spectroscopy (NIRS), Raman spectroscopy, Speckle, and surface plasmon resonance.

Patterns of electromagnetic radiation may be used in combination with non-optical data such as patient demographics, vital signs, in-vitro diagnostics, and/or any other input whose effect on the probability distribution is favorable to diagnostic performance. Optimization of computational models may also be based on patient demographics, other vital signs, or in vitro data, among others.

In one preferred form of the present invention, the method is implemented using a computational device, e.g., an appropriately programmed general purpose computer, a dedicated computer, etc., with the output of the computational device being displayed to the user.

In one preferred form of the present invention, optical sensors, thermistors, or other sensors might be added to the standard electrocardiography leads and the resulting anatomic or patterns utilized in the algorithm. These might be efficient as the clinicians are already placing leads in those locations.

In one preferred form of the present invention, the algorithm is discovered and optimized as an adjunct to resuscitation and treatment of systemic disease. As such, it would function as a goal for directing therapy. Such targeted therapeutics are often called theranostics.

By way of example, but not limited to, the diagnosis of shock, sepsis, congestive heart failure, hypoxia and/or other perfusion-threatening pathologic processes, potentially useful patterns might include:

1. The axial-acral distribution of measurements.
2. The change in measurements over time.
3. Maintenance of normal cephalic and/or central oxygenation, energetics, and/or perfusion in comparison with the extremities.
4. Maintenance of normal deep visceral oxygenation, energetics and/or perfusion in comparison with the extremities.
5. An algorithmic pattern incorporating anatomic, temporal, and alternative methods of sensing such as perfusion, oxygenation, and energetics.
6. Multiplex measurement of multiple visceral organs showing sparing for the organ (such as the brain and heart) in comparison to axial musculature or skin.
7. during successful resuscitation, the above patterns, such as described above, might be expected to be reversed and could be used in evaluating the adequacy of treatment.
8. Patterns, such as described above, may have improved diagnostic accuracy when adapted based on laboratory patterns such as in vitro diagnostic measurements of molecules related to perfusion and oxygen utilization, such as lactate.

OTHER PUBLICATIONS INCORPORATED IN THE CURRENT APPLICATION BY REFERENCE

Cohn, J. N. "Blood pressure measurement in shock. Mechanism of inaccuracy in auscultatory and palpatory methods." *JAMA* 199.13 (1967): 118-22.

Jobsis, F. F. "Noninvasive, infrared monitoring of cerebral and myocardial oxygen sufficiency and circulatory parameters." *Science* 198.4323 (1977): 1264-67.

Kato, K. "Algorithm for in vitro diagnostic multivariate index assay." *Breast Cancer* 16.4 (2009): 248-51.

Lewis, S. B., et al. "Cerebral oxygenation monitoring by near-infrared spectroscopy is not clinically useful in patients with severe closed-head injury: a comparison with jugular venous bulb oximetry." *Crit Care Med.* 24.8 (1996): 1334-38.

Soller, B. R., et al. "Noninvasively determined muscle oxygen saturation is an early indicator of central hypovolemia in humans." *J. Appl. Physiol* (1985.) 104.2 (2008): 475-81.

MODIFICATIONS

It will be understood that many changes in the details, materials, steps and arrangements of elements, which have been herein described and illustrated in order to explain the nature of the invention, may be made by those skilled in the art without departing from the scope of the present invention.

Since many modifications, variations and changes in detail can be made to the described preferred embodiment of the invention, it is intended that all matters in the foregoing description and shown in the accompanying drawing be interpreted as illustrative and not in a limiting sense. Thus, the scope of the invention should be determined by the appended claims and their legal equivalents.

Now that the invention has been described,

What is claimed is:

1. A method for determining the current or future probability of shock, comprising:
    measuring the optical and electromagnetic properties of tissue at multiple physiologically distinct locations on or within the patient's body;
    utilizing the anatomic, or anatomic and temporal, patterns of the measured tissue properties, with or without other variables, in a multiparametric algorithm or equation that is predictive or diagnostic of shock; and
    transforming the output results of the algorithm to a uniplex numerical or visual scale or index that is a probabilistic indicative of the current or future probability of a systemic medical condition.

2. A method for discovery and development of clinically useful synthetic biomarkers indicative of the current or future probability of shock, comprising:
    measuring the optical or electromagnetic properties of tissue at multiple physiologically distinct locations on or within the body in the setting of experimentally induced, clinically occurring shock, shock mimics, or normals;
    using known machine learning techniques to derive a multiparametric prognostic or diagnostic algorithm that includes, among other variables, anatomic, or anatomic and temporal, patterns of optical, electromagnetic, or physical measurements, such that the algorithm has better clinical performance than any of the input parameters individually;
    optimizing the algorithm iteratively using additional clinical data sets, clinical classifiers, along with patient characteristics and laboratory derived measurements as needed; and
    transforming the output results of the algorithm to a uniplex numerical or visual scale or index that is a probabilistic indicative of the current or future probability of a systemic medical condition.

3. A method according to claim 1 or 2, further comprising the algorithm being developed or utilized as a therapeutic adjunct for the treatment of shock, and would function as a goal for directing therapy.

4. A method according to claim 1 or 2, further comprising one or more of the tissue state measurements being obtained after administration of at least one of physical, chemical, biologic or pharmacologic agents.

5. A method according to claim 1 or 2, further comprising the performance of the algorithm being user modifiable so as to optimize a combination of sensitivity, specificity, positive predictive value, negative predictive value, receiver operatory characteristic curves or the time before shock becomes clinically manifest.

6. A method according claim 1 or 2, further comprising incorporation of the optimized algorithm, with or without other refinements, and along with associated numerical, visual scale or indices, into a stand-alone or pre-existing diagnostic or monitoring system.

7. A method according claim 1 or 2, further comprising use of one or more physical properties of tissue, such as temperature, density, weight, hydration state, transmission of sound and any combination of the foregoing, in the algorithm.

8. A method according to claim 1 or 2, wherein at least one of the optical measurements comprise near infra-red spectroscopy (NIRS), Raman spectroscopy, speckle, or surface plasmon resonance.

9. A method according to claim 1 or 2, further comprising additional optimization of the algorithm or its result by inclusion of pre-existing or laboratory technologies as inputs to the machine learning process.

10. A method according to claim 1 or 2, further comprising additional optimization of the algorithm or its result by inclusion of patient, clinical, hospital or epidemiology data as inputs to the machine learning process.

11. A method according to claim 1 or 2, wherein a component of the anatomic pattern is depth below the skin, or distance from the sensor, on or within the body.

12. A method according to claim 2, further comprising use of multiple classifiers, each possibly weighted differently, in development of the algorithm, so as to optimize its clinical performance.

13. A method according to claim 1 or 2, wherein at least one of the electromagnetic or optical measurements is indicative of cardiac function, such as the electrocardiogram, heart rate, cardiac output or ventricular stroke volume.

14. A method according to claim 1 or 2, wherein at least one of the optical measurements is indicative of tissue oxygen or energy status.

15. A method according to claim 1,
wherein the category of disease is toxic shock;
wherein the multiplicity of the optical and electromagnetic properties are selected from the group consisting tissue oxygen, tissue perfusion, tissue pH or any combination thereof;
wherein the multiplicity of physiologically distinct locations are selected from the group consisting of cephalic, ocular, oral, truncal, appendicular or any combination thereof; and,
wherein the multiplicity of anatomic, or anatomic and temporal patterns are selected from the group consisting of appendicular earlier, appendicular intermediate, appendicular later, truncal earlier, truncal intermediate, truncal later, cephalic earlier, cephalic intermediate, cephalic later, ocular earlier, ocular intermediate, ocular later, oral earlier, oral intermediate, oral later, or any combination thereof.

* * * * *